United States Patent

Kalopissis et al.

[11] 4,007,747
[45] Feb. 15, 1977

[54] N-MONOSUBSTITUTED INDOANILINES AS DYESTUFFS FOR KERATINIC FIBERS

[75] Inventors: Grégoire Kalopissis, Neuilly-sur-Seine; Andrée Bugaut, Boulogne-sur-Seine; Francoise Estradier, Paris, all of France

[73] Assignee: Societe Anonyme dite: L'Oreal, Paris, France

[22] Filed: Dec. 9, 1974

[21] Appl. No.: 530,975

[30] Foreign Application Priority Data

Dec. 12, 1973  Luxembourg .................. 68988

[52] U.S. Cl. .......................... 132/7; 8/10; 8/10.2; 8/11; 260/247.5 R; 260/396 N; 260/558 A; 260/562 N; 260/573; 260/574; 260/577; 260/247.2 A; 8/10.1; 260/293.76; 260/293.79

[51] Int. Cl.² .................. A61K 7/13; A45D 7/02

[58] Field of Search .............. 8/10, 10.1, 11, 10.2; 260/396 N, 247.5 R; 132/7

[56] References Cited

UNITED STATES PATENTS

| | | | |
|---|---|---|---|
| 2,455,169 | 11/1948 | Glass et al. ............. | 96/100 X |
| 3,185,567 | 5/1965 | Rogers .................. | 96/100 X |
| 3,342,597 | 9/1967 | Harnish et al. .......... | 96/100 X |

OTHER PUBLICATIONS

Vittum et al. I, Journal of the American Chemical Society, vol. 68, pp. 2235-2239, (1946).
Vittum et al. II, Journal of the American Chemical Society, vol. 69, pp. 152-155, (1947).

Primary Examiner—Leonard Schenkman
Assistant Examiner—Vera C. Clarke
Attorney, Agent, or Firm—Cushman, Darby & Cushman

[57] ABSTRACT

New dyestuffs are described for keratinic fibers which produce particularly luminous shades without the need for an oxidizing agent. These dyestuffs have the formula:

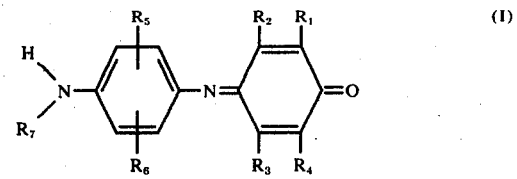

or a tautomeric form thereof wherein each of $R_1$ and $R_4$, which may be identical or different, represents a member selected from hydrogen, halogen, alkyl having 1 to 6 carbon atoms, alkoxy having 1 to 6 carbon atoms, acylamino and ureido;

each of $R_2$ and $R_3$, which may be identical or different, represents a member selected from hydrogen, halogen, alkyl having 1 to 6 carbon atoms, alkoxy having 1 to 6 carbon atoms, amino, N-alkylamino, N-(hydroxyalkyl)-amino, N-(carbamyl-alkyl)-amino, acylamino and ureido, each of said alkyls containing 1 to 6 carbon atoms;

each of $R_5$ and $R_6$, which may be identical or different, represents a member selected from hydrogen, halogen, alkyl containing 1 to 6 carbon atoms and alkoxy containing 1 to 6 carbon atoms, with the proviso that when $R_5$ and $R_6$ are both other than hydrogen at least one is in a meta-position relative to the $NHR_7$ group; and $R_7$ represents a member selected from alkyl, hydroxyalkyl, acylaminoalkyl, mesylaminoalkyl, carbamylalkyl, aminoalkyl, piperidinoalkyl and morpholinoalkyl, each of said alkyls containing 1 to 6 carbon atoms.

16 Claims, No Drawings

N-MONOSUBSTITUTED INDOANILINES AS DYESTUFFS FOR KERATINIC FIBERS

The present invention relates to indoanilines in which the amino group in the 4'-position is monosubstituted.

It is known to dye keratin fibers, more particularly living human hair, by applying to the hair, in the presence of an oxidizing agent such as hydrogen peroxide, added at the time of use, a dyeing composition comprising a mixture, in a suitable cosmetic carrier, of compounds belonging to each of two categories. The first category of compounds, generally called "oxidation bases", comprises mainly para-phenylene-diamines or para-amino-phenols which lead, on oxidation, to para-benzoquinonediimines or to para-benzoquinone-monoimines. The second category of compounds, generally called "coupling agents", comprises meta-amino-phenols, meta-acetylamino-phenols, meta-diamines and meta-diphenols. They are compounds with which the benzoquinonemono or di-imines will react to give rise to dyestuffs called, depending on their structure, indophenols, indoanilines or indamines.

These dyestuffs, from which a range of exceptionally rich shades can be obtained, are primarily noted for the luminous nature and for the rich sheen attainable therewith. However, when a complex dyeing composition is used, that is to say a composition which comprises several bases and several coupling agents, it is often very difficult to predict the contribution which each possible combination of oxidation base and coupling agent will make to the final shade. In other words, firstly, it is very difficult at the start to make an exact prediction as to the final shade, and, secondly, for a given dyeing composition, it is not often easy to be certain of perfect reproducibility. These difficulties are increased by the fact that various side reactions change the final shade. Examples of such side reactions are the formation of compounds of the Bandrowsky base type from the oxidation bases, the recondensation of a molecule of oxidation base with certain indophenols or with certain indoanilines or indamines and the formation of quinones.

An object of the present invention is to provide a process for dyeing keratin fibers, and particularly living human hair, which does not require the addition of an oxidizing agent at the time of use. The present invention also relates to the dyes and dye compositions for use in said process.

The objects of the present invention can be achieved by using certain novel indoanilines which possess the advantage of being able to give a very particularly rich range of extremely luminous shades of excellent aesthetic quality.

It has been found that by varying the nature of the substituent in the 4'-position it is possible to change various characteristics of such dyes, in particular their solubility, affinity and compatibility. Thus, increased solubility can be achieved by introducing a hydroxyalkyl or sulphoalkyl substituent, while the solubility of the dye in an alkaline medium can be improved by introducing a mesylaminoalkyl substituent. The affinity of the dye for keratin fibers can be increased by introducing an aminoalkyl substituent.

The present invention provides a N-monoalkyl-amino-indoaniline of the formula (I)

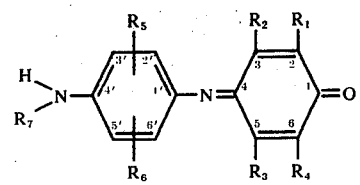

wherein
each of $R_1$ and $R_4$, which may be identical or different, represents hydrogen, halogen, lower alkyl, lower alkoxy, acylamino or ureido;
each of $R_2$ and $R_3$, which may be identical or different, represents hydrogen, halogen, lower alkyl, lower alkoxy, amino, N-(lower alkyl)-amino, N-[hydroxy-(lower alkyl)]-amino, N-[carbamyl-(lower alkyl)]-amino, acylamino or ureido;
each of $R_5$ or $R_6$, which may be identical or different, represents hydrogen, halogen, lower alkyl or lower alkoxy, with the proviso that $R_5$ and $R_6$ can occupy any two free positions but when they are both other than a hydrogen, at least one of the two occupies a meta-position relative to the —$NHR_7$ group; and
$R_7$ represents unsubstituted lower alkyl or substituted lower alkyl, and in particular hydroxy-(lower alkyl), acylamino-(lower alkyl), mesylamino-(lower alkyl), carbamyl(lower alkyl), amino-(lower alkyl), piperidino-(lower alkyl) or morpholino(lower alkyl).

By "lower" alkyl or "lower" alkoxy is meant alkyl or alkoxy containing 1 to 6, preferably 1 to 4, carbon atoms.

The invention also relates to the tautomeric form of the compounds of formula (I), especially those of the formula

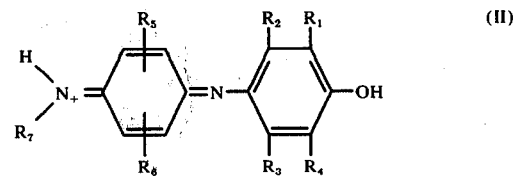

or in the case where $R_3$ denotes an optionally monosubstituted amino group, those of the formula

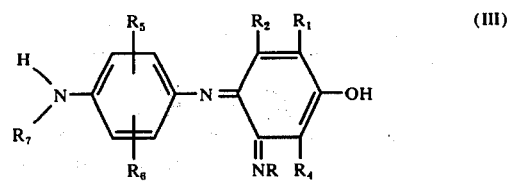

wherein R represents hydrogen, lower alkyl, hydroxy-(lower alkyl) or carbamyl-(lower alkyl).

The compounds of this invention can be prepared by condensing a compound of the formula:

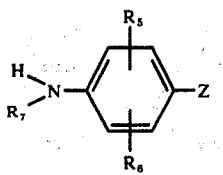

(IV)

or an addition salt thereof, on a phenolic compound of the formula

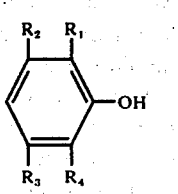

(V)

or an addition salt thereof.

In formula (IV), Z represents —$NH_2$ or —NO. When Z denotes —$NH_2$, $R_1$ to $R_7$ are as defined above for formula (I). When Z denotes —NO, $R_1$ to $R_6$ are as defined above for formula (I) and $R_7$ represents unsubstituted lower alkyl.

When Z denotes —$NH_2$, the condensation is suitably carried out in an aqueous, aqueous-alcoholic or aqueous-acetone medium, at an alkaline pH generally greater than 8 and in the presence of an oxidizing agent, for example, ammonium persulphate, potassium ferricyanide or hydrogen peroxide. Generally the alkaline pH is obtained with ammonia or with an alkaline carbonate preferably sodium carbonate and the reaction is carried out at a temperature from about 0° to 25° C.

When Z denotes —NO, the condensation is generally carried out at a temperature of about 50° C, in an aqueous-ethanolic medium which is neutral or has been rendered alkaline by adding a dilute solution of a base preferably sodium hydroxide.

The present invention also provides a dyeing composition for keratin fibers, and particularly for living human hair, which contains in a compatible vehicle, usually an aqueous or aqueous-alcoholic solution, at least one compound of the present invention.

These dyeing compositions generally contain 0.001 to 2% of compound of formula (I), relative to the total weight of the composition.

The dyeing composition according to this invention can contain the idoanilines of formula (I) as the only dyestuff. It is, however, possible to mix the dyestuffs of this invention with other dyestuffs usually employed for dyeing hair, for example nitrobenzene, azo, anthraquinone, indamine, indophenol and/or other indoaniline dyestuffs. Generally when a dye other than the dye of the present invention is employed, the said other dye or dyes is present in amounts of about 0.001 to 1 percent by weight of said composition.

The compositions according to the present invention are generally in the form of an aqueous or aqueous-alcoholic solution containing one or more compounds of formula (I), which may or may not be mixed with other dyestuffs. They can however also contain, for example, thickeners and be in the form of creams or gels. Suitable thickeners which can be used include cellulosic derivatives such as methyl-cellulose, hydroxyethyl-cellulose and carboxymethyl-cellulose; acrylic polymers such as the sodium salt of polyacrylic acid and ethanolamides of fatty acids, preferably mono- or diethanolamide of fatty acids of copra and carboxyvinyl polymers. The thickener can be present, for instance, in amounts of about 0.5 to 7 percent by weight of said composition.

The dyeing composition can contain, as solvents, water, lower alkanols, for example ethanol or isopropanol, and polyhydric alcohols such as glycols, for example ethylene glycol, propylene glycol, butyl glycol, diethylene glycol and the monomethyl ether of diethylene glycol. The solvent is generally present in amounts of about 1 to 60 percent by weight of said composition.

The compositions can also contain various adjuvants usually employed in cosmetics for the hair, such as wetting agents, for example oxyethylenated alkylphenols and oxyalkylenated fatty alcohol sulphates and sulphonates, dispersing agents, swelling agents, penetrating agents, softeners or perfumes. They can, moreover, be packaged in aerosol containers in the presence of a propellant gas. Suitable propellant gases include nitrogen, nitrous oxide, volatile hydrocarbons such as butane, isobutane or propane, or, preferably, fluorinated hydrocarbons (sold under the name of "Freon") such as dichloridifluoromethane, 1,1-difluoro-methane, 1,2-dichloro-1,1,2,2-tetrafluoro-ethane or 1-chloro-1,1-difluoro-methane; mixtures of two or more hydrocarbons or fluorinated hydrocarbons can also be used.

The pH of the compositions, which can vary within wide limits, is generally from about 5 to 11 and preferably from 7 to 9. The pH can be adjusted by means of an alkali, for example ammonia, mono-, di- or triethanolamine, di- or tri- sodium phosphate, or sodium or potassium carbonate, or by means of an acid, for example acetic acid, lactic acid, phosphoric acid or citric acid.

The dyeing of keratin fibers, particularly living human hair, by means of the dyeing compositions according to the present invention can be carried out in the usual way by applying the composition to the fibers to be dyed, leaving it in contact therewith for about 5 to 30 minutes, and then rinsing the fibers and optionally washing them and drying them.

Depending on the nature of the substituents, the indoanilines of the present invention make it possible to obtain a very wide range of colors ranging from greens to violets via blues; only yellows and oranges are not represented. The dyeings obtained are notable for their luminous nature and their rich sheen, especially a pearly or metallic sheen.

When the compositions according to the invention are in the form of aqueous-alcoholic solutions, they can also contain a cosmetic resin, in which case they form what are commonly called colored wavesetting lotions, which can be applied to wet hair before setting it in waves. These compositions generally contain about 0.001 to 0.5% of a compound of formula (I).

Representative cosmetic resins which can be used in such wavesetting lotions according to this invention include such film-forming polymers as polyvinylpyrrolidone, copolymers of vinylpyrrolidone and vinyl acetate, copolymers of vinyl acetate and an unsaturated carboxylic acid such as crotonic acid, copolymers resulting from the copolymerization of vinyl acetate, crotonic acid and an acrylic or methacrylic ester, copolymers resulting from the copolymerization of vinyl acetate and an alkyl vinyl ether, copolymers resulting from the copolymerization of vinyl acetate, crotonic acid and a vinyl ester of an acid with a long carbon chain (i.e. more than 8 carbon atoms) or an allyl or methallyl ester of an acid with a long carbon chain, copolymers resulting from the copolymerization of an ester derived from an unsaturated alcohol and from an acid with a short carbon chain (i.e. not more than 8 carbon atoms), an unsaturated acid with a short chain and at least one ester derived from a saturated alcohol with a short chain and from an unsaturated acid, and copolymers resulting from the copolymerization of at least one unsaturated ester and at least one unsaturated acid.

Representative preferred resins include polyvinylpyrrolidone having a molecular weight of 10,000 to 360,000; copolymers comprising 10% of crotonic acid and 90% of vinyl acetate having a molecular weight of 10,000 to 70,000; copolymers of vinylpyrrolidone (VP) and vinyl acetate (VA) with a molecular weight of 30,000 to 200,000, the VP/VA ratio being from 30/70 to 70/30; copolymers of maleic anhydride and methyl vinyl ether, the specific viscosity of which, measured at 25° C as 1 g/100 ml solution in methyl ethyl ketone, is from 0.1 to 3.5 centipoises, the ethyl, isopropyl and butyl monoesters of copolymers of maleic anhydride and methyl vinyl ether; copolymers of maleic anhydride and butyl vinyl ether; terpolymers of methyl methacrylate (15–25%), stearyl methacrylate (25–35%) and dimethylaminoethyl methacrylate (52–62%), preferably quaternized, for example by means of dimethyl-sulphate, the viscosity of which, measured at the boiling point of the ether as 5% solution in dimethylformamide, is from 8 to 12 centipoises; and terpolymers of vinyl acetate (75–85%), allyl stearate (10–20%) and allyloxy-acetic acid (3–10%), the viscosity of which, measured at the boiling point of the ether as a 5% solution in dimethylformamide, is from 4.4 to 5 centipoises.

These resins are generally used in an amount from 1 to 3% by weight of the total weight of the composition.

The alcohols which are suitable for producing wavesetting lotions according to the invention are alcohols of low molecular weight, preferably ethanol or isopropanol. These alcohols are suitably employed in an amount from 20 to 70% by weight.

The wavesetting lotions according to the present invention can be employed in the usual way, by applying them to wet hair which has been washed and rinsed beforehand, constraining in a deformed state, for example by winding up on curlers and drying the hair.

The dye composition of the present invention can include a surface active agent as a carrier or as a thickening agent. Representative surface active agents that can usefully be employed include oxyethylenated alcohols, particularly oxyethylenated lauryl alcohol; partially sulfated oxyethylenated lauryl alcohol and preferably a mixture consisting of 19% lauryl alcohol oxyethylenated with 2 moles of ethylene oxide and 81% of the sodium sulfate salt of this same oxyethylenated alcohol; the alkaline or ammonium sulfate salts of long chain fatty alcohols, for example, ammonium lauryl sulfate; and oxyethylenated alkylphenols and preferably nonylphenol oxyethylenated with 4 or 9 moles of ethylene oxide per mole of alkylphenol. The surface active agent is generally employed in amounts of about 2 to 30 percent by weight of said composition.

The invention is illustrated by the following examples which are tabulated in Tables I, II, III and IV.

Examples pertaining to the preparation of the dyes of the present invention appear in Tables I and II. Table I which provides data concerning the characteristics of the prepared benzopquinoneimine dyes of this invention has columns numbered 1 through 9 inclusive. Column 1 indicates the number of the Example; Column 2 identifies the benzoquinoneimine prepared; Column 3 gives the melting point of the prepared benzoquinoneimine; Column 4 provides the empirical formula for the prepared benzoquinoneimine; and Columns 5 through 9 tabulate respectively the percentages of C, H, N, Cl and S in said dye. For each compound prepared, columns 5 through 9 carry two or three lines. The first line indicates the theoretical percentage of the indicated element corresponding to the empirical formula of column 4; line 2, and when provided, line 3 indicate the percentages found by analysis.

Table II which synopsizes the process by which the benzoquinones appearing in Table I are prepared, has eight columns numbered 1 and 10–16. Column 1 indicates, as in Table I, the number of the Example of preparation; Column 10 indicates the substituted aniline initial reactant; Column 11 identifies the substituted phenol initial reactant; Column 12 gives the molar ratio of the substituted phenol of Column 11 to the substituted aniline of Column 10; Column 13 identifies the reaction medium employed; Column 14 lists when appropriate the particular oxidizing agent used; Column 15 indicates, also when appropriate, the molar ratio of the oxidizing agent of Column 14 to phenol of Column 11; and Column 16 identifies the reaction temperature employed in degrees centigrade.

The benzoquinoneimines of Examples 1 to 8 are prepared by the reaction of a substituted nitroso aniline of the formula

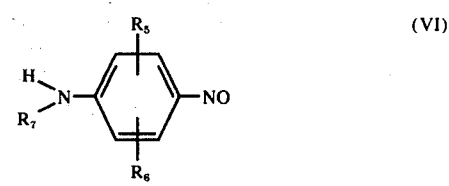

(VI)

on a substituted phenol of formula (V), in ethanol or a 1:1 ethanol-water mixture made alkaline by sodium hydroxide and in the absence of an oxidizing agent.

The benzoquinoneimines of Example 9 and following are prepared by the reaction of a substituted p-phenylenediamine (substituted aniline) of the formula (VII)

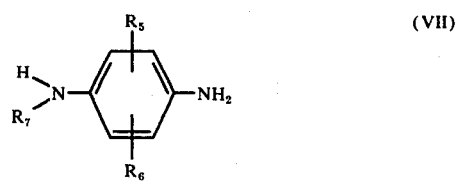

(VII)

on a substituted phenol of formula (V). The molar ratio of substituted phenol : substituted aniline can be between 1:0.5 and 1:1.2 and preferably between 1:0.65 and 1:1. The molar ratio of oxidizing agent : phenol is between 1:1 and 4:1 when there is employed, as the oxidizing agent, ammonium persulfate or potassium ferricyanide. This molar ratio however is from 8:1 when there is used, as the oxidizing agent, hydrogen peroxide. The latter is generally employed in the form of a 6 weight percent solution. The reaction medium comprises water, a lower alkanol, preferably ethanol, propanol or isopropanol, an acetone-water mixture or a lower alkanol-water mixture, both generally in a 1:1 volume ratio. The pH of the reaction medium is alkalinized to a pH of at least 8, preferably by the addition thereto of an alkalizing agent such as ammonia or an alkaline carbonate.

The Examples of use include not only examples of simple dye compositions which are tabulated in Table IV, but also of dye compositions containing a cosmetic film forming resin. The latter compositions are often referred to as hair setting lotions and are tabulated in Table III.

Table III contains 12 columns numbered from 11 to 22. Column 11 indicates the number of the Example of the hair setting lotion. The column carries a number preceded by the letter M. Column 12 indicates the number of the Example of preparation according to which is prepared the benzoquinoneimine used as the dye or the letter C followed by a number which represents another dye used in admixture with the benzoquinoneimine. The name of this additional dye appears at the bottom of the table. Column 13 indicates the amount of dye expressed in weight percent of the total weight of the composition. Columns 14–17 concern the cosmetic resin used. Column 14 indicates the name of the resin and column 15 its average molecular weight. Column 16 reports the viscosity of the resin in centipoises while Column 17 indicates the weight percent of the resin relative to the total weight of the composition. Columns 18 and 19 reveal, respectively, the name and the weight percent (relative to the total weight of the composition), of the alcohol used. Column 20 indicates the pH of the composition while Column 22 indicates the color obtained on the bleached hair (D) or 95% naturally white hair (B 95). This latter indication of the type of hair to which the composition is applied appears in column 21. In Column 14, the name of the resin, polymer or copolymer, is indicated by abbreviations. These abbreviations and their meaning are as follows: PVP = polyvinylpyrrolidone; VA/CA = copolymer of vinyl acetate and crotonic acid; VP/VA = copolymer of vinylpyrrolidone and vinyl acetate; and MM/StM/DEM = copolymer of methyl methacrylate (15–25%)/stearyl methacrylate (25–35%)/dimethylaminoethyl methacrylate (52–62%) quaternized with dimethyl sulfate.

The viscosity of the VP/VA copolymer is measured at 25° C in a 5% solution in ethanol. The viscosity of the terpolymer MM/StM/DEM is measured at the boiling point of ether (35° C) and at a concentration of 5% in dimethylformamide.

Table IV carries 12 columns numbered from 31 to 42. Column 31 indicates the number of the Example of the dye composition. This column carries a number preceded by the letter T. Column 32 indicates the number of the Example of preparation according to which is prepared the benzoquinoneimine used as the dye or the letter C followed by a number which represents another dye used in admixture with the benzoquinoneimine and for which the name appears at the bottom of the Table. Columns 34 and 35 indicate respectively the nature and the weight percent of the surface active agent used. Column 33 indicates the amount of dye employed, expressed in weight percent. Columns 36 and 37 indicate, respectively, the name and weight percent of the solvent used while Columns 38 and 39 indicate the name and weight percent of the adjuvant used. Column 40 indicates the pH of the composition and Column 42 indicates the color obtained on bleached hair (D) or on 95% naturally white hair (B 95). This latter indication of the type of hair to which the composition is applied appears in Column 41. All percents indicated are by weight of the total weight of the composition.

In Columns 34 and 38, the name of the surface active agent and various adjuvants are indicated by abbreviations, the meanings of which appear at the bottom of the Table.

TABLE I

| Ex. No. (1) | BENZOQUINONEIMINE (2) | Melting Point (°C)(3) | Empirical Formula (4) | C % (5) | H % (6) | N % (7) | Cl % (8) | S % (9) |
|---|---|---|---|---|---|---|---|---|
| 1 | N-[(4'-ethylamino)phenyl]-2-methyl-5-carbamylmethylamino benzoquinoneimine | 225 | $C_{17}H_{20}N_4O_2$ | 65.36 65.06 65.08 | 6.45 6.59 6.64 | 17.94 18.16 18.04 | | |
| 2 | N-[(4'-ethylamino-2'-methyl)phenyl]-2,6-dimethyl 3-amino benzoquinoneimine | 128 | $C_{17}H_{21}N_3O$ | 72.05 72.38 72.45 | 7.47 7.62 7.51 | 14.83 15.12 15.09 | | |
| 3 | N-[(4'-ethylamino-2'-methyl)phenyl]-2-methyl 5-amino benzoquinoneimine | 182 | $C_{16}H_{19}N_3O$ | 71.34 71.41 71.32 | 7.11 7.21 7.32 | 15.60 15.76 15.82 | | |
| 4 | N-[(4'-ethylamino)phenyl]-2-chloro-5-amino benzoquinoneimine | 184 | $C_{14}H_{14}N_3OCl$ | 60.98 61.07 60.94 | 5.09 5.17 5.14 | 15.25 15.24 15.34 | 12.87 12.92 13.90 | |
| 5 | N-[(4'-ethylamino-3'-methyl)phenyl-2,6-dimethyl-3-amino benzoquinoneimine | 147 | $C_{17}H_{21}N_3O$ | 72.05 71.78 71.67 | 7.47 7.42 7.53 | 14.83 15.04 14.65 | | |
| 6 | N-[(4'-ethylamino)phenyl]-2,6-dimethyl-3-amino benzoquinoneimine | 162 | $C_{16}H_{19}N_3O$ | 71.34 71.12 71.28 | 7.11 7.11 6.90 | 15.60 15.79 15.76 | | |
| 7 | N-[(4'-methylamino-2',5'-dimethyl)phenyl]-2,6-dimethyl-3-amino benzoquinoneimine | 210 | $C_{17}H_{21}N_3O$ | 72.05 71.94 | 7.47 7.77 | 14.83 14.81 | | |
| 8 | N-[(4'-methylamino)phenyl]-2-methyl-5-amino benzoquinoneimine | 162 | $C_{14}H_{15}N_3O$ | 69.69 68.52 68.57 | 6.27 6.33 6.39 | 17.42 17.62 17.55 | | |
| 9 | N-[(4'-methylamino-3'-methoxy)phenyl]-2,6-dimethyl benzoquinoneimine | 156 | $C_{16}H_{18}N_2O_2$ | 71.09 70.86 70.79 | 6.71 6.83 6.76 | 10.36 10.42 10.49 | | |

4,007,747

TABLE I-continued

| | | | | | | | |
|---|---|---|---|---|---|---|---|
| 10 | N-[(4'-methylamino)phenyl]-2,6-dimethyl 3-amino benzoquinoneimine | 166 | C₁₅H₁₇N₃O MW = 255 (1) 251 (2) | 70.56 70.75 70.41 | 6.71 6.67 6.68 | 16.46 16.49 16.52 | |
| 11 | N-[(4'-ethylamino 2'-methyl)phenyl] 3-chloro 6-ureido benzoquinoneimine | 222 | C₁₆H₁₇N₄O₂Cl | 57.74 57.26 57.30 | 5.11 5.04 5.21 | 16.87 16.61 16.71 | 10.67 10.41 10.47 |
| 12 | N-[(4'-butylamino 3'-chloro)phenyl]-2-methyl 5-acetylamino benzoquinoneimine | 87 | C₁₉H₂₂N₃O₂Cl | 63.42 63.06 63.14 | 6.16 6.16 6.23 | 11.67 11.87 11.73 | 9.85 9.69 9.66 |
| 13 | N-[(4'-ethylamino 2'-methyl)phenyl]-3-ureido benzoquinoneimine | 212 | C₁₆H₁₈N₄O₂ | 64.41 64.29 64.58 | 6.08 6.25 6.09 | 18.78 18.62 18.62 | |
| 14 | N-[(4'-methylamino)phenyl]-2,6-dimethyl 3-acetylamino benzoquinonemine | 158 | C₁₇H₁₉N₃O₂ | 68.66 68.29 68.32 | 6.44 6.57 6.58 | 14.13 14.25 14.34 | |
| 15 | N-[(4'-ethylamino 2'-methyl)phenyl]-3-chloro 6-acetylamino benzoquinoneimine | 162 | C₁₇H₁₈N₃O₂Cl | 61.54 60.98 61.22 | 5.43 5.26 5.25 | 12.67 12.97 12.86 | 10.71 10.39 10.45 |
| 16 | N-[(4'-ethylamino)phenyl]-2-methyl-5-acetyl-amino benzoquinoneimine | 100 | C₁₇H₁₉N₃O₂ | 68.66 68.12 68.41 | 6.44 6.44 8.66 | 14.13 13.98 13.94 | |
| 17 | N-[(4'-butylamino-3'-chloro)phenyl] 3-acetylamino benzoquinoneimine | 124 | C₁₈H₂₀N₃O₂Cl | 62.52 62.35 62.29 | 5.80 6.03 6.04 | 12.15 12.21 12.09 | 10.25 10.40 10.17 |
| 18 | N-[(4'-ethylamino)phenyl]-2-chloro 5-acetyl-amino benzoquinoneimine | 198 | C₁₆H₁₆N₃O₂Cl | 60.47 59.98 59.85 | 5.04 4.97 5.06 | 13.22 13.21 13.17 | |
| 19 | N-[(4'-ethylamino-3'chloro)phenyl] 2-methyl 5-acetylamino benzoquinoneimine | 144 | C₁₇H₁₈N₃O₂Cl | 61.53 61.57 61.28 | 5.46 5.61 5.51 | 12.66 12.53 12.86 | 10.68 10.79 10.65 |
| 20 | N-[(4'-(β-acetylamino-ethyl)amino phenyl]3-methyl 6-chloro benzoquinoneimine | 126 | C₁₇H₁₈N₃O₂Cl | 61.54 61.24 61.32 | 5.46 5.60 5.54 | 12.64 12.55 12.47 | 10.70 10.59 10.48 |
| 21 | N-[(4'-(β-hydroxyethyl)amino phenyl] 2-bromo-5-amino benzoquinoneimine | 206 | C₁₄H₁₄N₃O₂Br | 50.00 50.12 50.24 | 4.16 4.35 4.28 | 12.50 12.60 12.36 | 23.84 23.62 23.65 |
| 22 | N-[(4'-β-hydroxyethylamino-3'-methyl)phenyl] 2-methyl-5-acetylamino benzoquinoneimine | 242 | C₁₈H₂₁N₃O₃ | 66.03 65.85 65.87 | 6.47 6.65 6.44 | 12.84 12.93 13.06 | |
| 23 | N-[(4'-β-morpholinoethylamino)phenyl]-2-chloro 5-acetylamino benzoquinoneimine | 180 | C₂₀H₂₃N₄O₃Cl | 59.62 59.03 58.98 | 5.71 5.61 5.87 | 13.91 14.06 14.18 | 8.81 8.72 8.74 |
| 24 | N-[(4'-β-morpholinoethylamino)phenyl]-3-ureido benzoquinoneimine | 178 | C₁₉H₂₃N₅O₃ | 61.77 61.05 61.28 | 6.28 6.26 6.22 | 18.96 18.82 18.75 | |
| 25 | N-[(4'-β-mesylamino-ethylamino)phenyl]-2-methyl 5-acetylamino benzoquinoneimine | 126 | C₁₈H₂₂N₄O₄S | 55.38 55.02 55.17 | 5.68 5.97 5.82 | 14.35 14.35 14.43 | |
| 26 | N-[(4'-β-acetylaminoethylamino)phenyl]-3-chloro-6-ureido benzoquinoneimine | 230 | C₁₇H₁₈N₅O₃Cl | 54.33 54.22 54.48 | 4.80 5.11 5.08 | 18.64 18.67 18.55 | |
| 27 | N-[(4'-β-hydroxyethylamino-3'-methoxy)phenyl] 2-methyl-5-amino benzoquinoneimine | 150 | C₁₆H₁₉N₃O₃ | 63.77 63.81 64.02 | 6.36 6.53 6.65 | 13.95 14.02 14.19 | |
| 28 | N-[(4'-β-mesylaminoethylamino-3'-methyl)phenyl]-2,6-dimethyl-5-acetylamino benzoquinoneimine | 148 | C₂₀H₂₆N₄O₄S | 57.40 57.52 57.23 | 6.26 6.24 6.27 | 13.39 13.53 13.45 | 7.64 7.66 7.44 |
| 29 | N-[(4'-β-acetylaminoethylamino-3'-methoxy)phenyl]-2,6-dimethyl-5-amino benzoquinoneimine | 183 | C₁₉H₂₄N₄O₃ | 64.02 63.87 63.74 | 6.79 6.58 6.70 | 15.72 15.51 15.20 | |
| 30 | N-[(4'-β-mesylamino ethylamino-3'-chloro)phenyl]-2-methyl-5-acetylamino benzoquinoneimine | 244 | C₁₈H₂₁N₄O₄S Cl | 50.88 50.71 50.77 | 4.98 5.20 5.20 | 13.18 13.36 13.42 | 7.54 7.26 7.38 |
| 31 | N-[(4'-β-acetylamino-3'-chloro)phenyl]-2,6-dimethyl benzoquinoneimine | 161 | C₁₈H₂₀N₃O₂ Cl | 62.51 62.29 62.36 | 5.79 5.80 5.94 | 12.15 12.21 12.10 | 10.27 10.23 10.38 |

TABLE I-continued

| Ex. No. | BENZOQUINONEIMINE | Melting Point (°C) | Empirical Formula | C % | H % | N % | Cl % |
|---|---|---|---|---|---|---|---|
| 32 | N-[(4'-β-hydroxyethylamino-3'-methoxy)phenyl]-2,6-dimethyl-5-amino benzoquinoneimine | 165 | $C_{17}H_{21}O_3N_3$ | 64.74 64.66 } 64.50 } | 6.71 6.78 } 6.78 } | 13.33 13.17 } 13.15 } | |
| 33 | N-[(4'-βhydroxyethylamino-3'-methoxy)phenyl]2,6-dimethyl-5-acetylamino benzoquinoneimine | 110 | $C_{19}H_{23}O_4N_3 \cdot H_2O$ | 60.79 60.53 } 60.45 | 6.71 6.58 } 6.61 } | 11.19 11.31 } 11.36 } | |
| 34 | N-[(4'-β-hydroxyethylamino-3'-chloro)phenyl]-3-chloro 6-acetylamino benzoquinoneimine | 144 | $C_{16}H_{15}N_3O_3Cl_2$ | 52.19 52.05 } 51.93 | 4.10 4.42 } 4.38 } | 11.41 11.52 } 11.36 } | 19.26 19.16 } 19.23 } |
| 35 | N-[(4'-β-aminoethylamino-3'-methyl-6'-methoxy)phenyl]-2,6-dimethyl-3-amino benzoquinoneimine | 168 | $C_{18}H_{24}N_4O_2$ | 65.83 65.12 } 65.24 | 7.37 7.03 } 7.17 } | 17.06 16.98 } 16.84 } | |
| 36 | N-[(4'-β-mesylaminoethylamino-3'-methyl)phenyl]-2-methyl-5-acetylamino benzoquinoneimine | 242 | $C_{19}H_{24}N_4O_4S$ | 56.43 56.41 } 56.58 | 5.98 6.04 } 6.21 } | 13.86 14.07 } 14.12 } | 7.91 7.74 } 7.84 } |
| 37 | N-[(4'β-acetylaminoethylamino-3'-methyl)phenyl]-3-ureido benzoquinoneimine | 222 | $C_{18}H_{21}N_5O_3$ | 60.83 60.66 } 60.57 | 5.96 6.16 } 5.97 } | 19.71 19.61 } 19.70 } | |
| 38 | N-[(4'-β-carbamylmethylamino-3'-methyl)phenyl]-2,6-dimethyl-3-acetylamino benzoquinoneimine | 240 | $C_{19}H_{22}N_4O_3$ | 64.39 64.98 } 64.87 | 6.26 6.47 } 6.53 } | 15.81 15.45 } 15.78 } | |
| 39 | N-[(4'-γ-morpholinopropylamino-3'-chloro)phenyl]-3-chloro-6-acetylamino benzoquinoneimine | 214 | $C_{21}H_{24}N_4O_3Cl_2$ MW 451 (1) 448 (2) | 55.87 55.58 | 5.36 5.56 | 12.41 12.56 | 15.74 15.78 |
| 40 | N-[(4'-methylamino)phenyl]-2,6-dimethyl benzoquinoneimine | 132 | $C_{15}H_{16}N_2O$ MW 240 (1) 239 (2) | 74.97 4.68 | 6.71 6.91 | 11.66 11.44 | |
| 41 | N-[(4'-methylamino-3'-methyl)phenyl]-2,6-dimethyl-3-acetylamino benzoquinoneimine | 160 | $C_{18}H_{21}N_3O_2$ | 69.43 69.36 | 6.80 6.73 | 13.50 13.28 | |
| 42 | N-[(4'-methylamino-2'-methyl)phenyl]-2,6-dimethyl 3-acetylamino benzoquinoneimine | 218 | $C_{18}H_{21}N_3O_2$ | 69.43 69.60 | 6.80 6.68 | 13.50 13.27 | |
| 43 | N-[(4'-methylamino-2'-methyl)phenyl]-2,6-dimethyl benzoquinoneimine | 138 | $C_{16}H_{18}N_2O$ | 75.56 75.69 | 7.13 7.12 | 11.02 11.11 | |
| 44 | N-[(4'-methylamino-2-'-methyl)phenyl]-2,6-dimethyl benzoquinoneimine | 129.5 | $C_{16}H_{18}N_2O$ MW 254 (1) 260 (2) | 75.56 75.61 | 7.13 7.01 | 11.02 11.32 | |
| 45 | N-[(4'-β-hydroxyethylamino-2'-methoxy)phenyl]-2-methyl-5-acetylamino benzoquinoneimine | 163 | $C_{18}H_{21}N_3O_4$ | 62.96 62.76 | 6.16 6.31 | 12.24 12.24 | |
| 46 | N-[(4'-β-acetylaminoethylamino-3'-chloro)phenyl]-3-methoxy benzoquinoneimine | 156 | $C_{17}H_{18}N_3O_3Cl$ | 58.70 58.41 } 58.56 | 5.18 4.97 } 5.04 } | 12.08 12.20 } 12.17 } | |
| 47 | N-[(4'-βmesylaminoethylamino)phenyl]-2,6-dimethyl-3-acetylamino benzoquinoneimine | 157 | $C_{19}H_{24}N_4O_4S$ | 56.43 56.30 | 5.98 6.00 | 13.86 13.98 | 8.07 7.91 |
| 48 | N-[(4'-β-hydroxyethylamino)phenyl[-2-methyl 5-acetylamino benzoquinoneimine | 162 | $C_{17}H_{19}N_3O_3$ | 65.16 65.16 | 6.11 6.25 | 13.41 13.63 | |
| 49 | N-[(4'-β-hydroxyethylamino-3'-methoxy)phenyl]-2,6-dimethyl benzoquinoneimine | 166 | $C_{17}H_{20}N_2O_3$ | 67.98 67.90 | 6.71 6.72 | 9.33 9.30 | |

(1) Molecular weight calculated
(2) Molecular weight determined by potentiometric titration in acetic acid using perchloric acid

| Ex. No. (1) | BENZOQUINONEIMINE (2) | Melting Point (°C)(3) | Empirical Formula (4) | C % (5) | H % (6) | N % (7) | Cl % (8) |
|---|---|---|---|---|---|---|---|
| 50 | N-[(4'-γ-morpholinopropylamino-3'-chloro)phenyl]-2-bromo-5-amino benzoquinoneimine | 212 | $C_{19}H_{22}N_4Br_2ClO_2$ | 50.17 50.10 | 4.85 5.06 | 12.35 12.65 | |
| 51 | N-[(4'-methylamino-2'-methoxy)phenyl]-2,6-dimethyl-5-acetylamino benzoquinoneimine | 249 | $C_{18}H_{21}N_3O_3$ | 66.03 65.84 | 6.47 6.52 | 12.84 12.79 | |
| 52 | N-[(4'-methylamino-2'-methoxy)phenyl]-2-methyl-5-acetylamino benzoquinoneimine | 204 | $C_{17}H_{19}N_3O_3$ | 65.16 64.92 | 6.11 6.19 | 13.41 13.34 | |
| 53 | N-[(4'-methylamino 3'-methoxy)phenyl]-2,6-dimethyl-5-amino benzoquinoneimine | 195 | $C_{16}H_{19}N_3O_2$ | 67.34 67.20 | 6.71 6.71 | 14.73 14.99 | |
| 54 | N-[(4'-methylamino 2'-methoxy)phenyl]-2-methyl-5-amino benzoquinoneimine | 178 | $C_{16}H_{17}N_3O_2 \cdot 0.5H_2O$ | 64.28 64.26 | 6.42 6.61 | 15.00 14.87 | |
| 55 | N-[(4'-methylamino-3'-chloro)phenyl]-2-methyl-5-acetylamino benzoquinoneimine | 206 | $C_{16}H_{16}Cl\,N_3O_2$ | 60.45 60.35 | 5.07 5.23 | 13.22 13.31 | |
| 56 | N-[-(4'-methylamino-3'-chloro)phenyl]-2,6-dimethyl-5-acetylamino benzoquinoneimine | 166 | $C_{17}H_{18}Cl\,N_3O_2$ | 61.53 61.61 | 5.47 5.62 | 12.66 12.51 | 10.68 10.53 |

TABLE I-continued

| | | Melting Point | Empirical Formula | C % | H % | N % | Cl % |
|---|---|---|---|---|---|---|---|
| 57 | N-[(4'-methylamino-3'-chloro)phenyl]-2,6-dimethyl benzoquinoneimine | 127 | $C_{15}H_{15}ClN_2O$ | 65.58<br>65.41 | 5.50<br>5.60 | 10.19<br>10.24 | 12.90<br>12.90 |
| 58 | N-[(4'-methylamino-3'-chloro)phenyl]-2,6-dimethyl-5-amino benzoquinoneimine | 165 | $C_5H_{16}ClN_3O$<br>$.0.5H_2O$ | 60.30<br>60.64 | 5.70<br>5.70 | 14.01<br>14.07 | 11.91<br>11.98 |
| 59 | N-[(4'-methylamino-3'-chloro)phenyl]-2-methyl-5-amino benzoquinoneimine | 174 | $C_{14}H_{14}ClN_3O$ | 60.98<br>61.17 | 5.11<br>5.32 | 15.24<br>15.10 | 12.86<br>12.67 |
| 60 | N-[(4'-methylamino-2'-chloro)phenyl]-2,6-dimethyl-5-acetylamino benzoquinoneimine | 235 | $C_{17}H_{18}ClN_3O_2$ | 61.53<br>61.26 | 5.47<br>5.56 | 12.66<br>12.90 | 10.68<br>10.47 |
| 61 | N-[(4'-methylamino-2'-chloro)phenyl]-2,6-dimethyl-5-amino benzoquinoneimine | 182 | $C_{15}H_{16}N_3OCl$ | 62.16<br>61.92 | 5.56<br>5.71 | 14.50<br>14.30 | 12.23<br>12.05 |
| 62 | N-[(4'-methylamino-2'chloro)phenyl]-2-methyl-5-amino benzoquinoneimine | 180 | $C_{14}H_{14}N_3OCl$ | 60.98<br>60.83 | 5.11<br>4.99 | 15.24<br>15.10 | 12.86<br>12.74 |
| 63 | N-[(4'-methylamino-2'-chloro)phenyl]-2-methyl-5-acetylamino benzoquinoneimine | 234 | $C_{16}H_{16}N_3O_2Cl$ | 60.47<br>60.42 | 5.07<br>5.29 | 13.22<br>13.18 | |
| 64 | N-[(4'-methylamino-3'-methoxy)phenyl]-2,6-dimethyl-5-acetylamino benzoquinoneimine | 120<br>158(1) | $C_{18}H_{21}N_3O.0.5H_2O$ | 64.28<br>64.52 | 6.54<br>6.78 | 12.50<br>12.69 | |
| 65 | N-[(4'-methylamino-2'-chloro)phenyl]-2-methyl-5-β hydroxyethylamino benzoquinoneimine | 190 | $C_{16}H_{18}N_3O_2Cl$ | 60.09<br>60.15 | 5.67<br>5.86 | 13.14<br>13.31 | 11.11<br>11.19 |
| 66 | N-[(4'-methylamino-2'-methoxy)phenyl]-2,6-dimethyl benzoquinoneimine | 152 | $C_{16}H_{18}N_2O_2$ | 71.09<br>71.40 | 6.71<br>6.91 | 10.36<br>10.15 | |
| 67 | N-[(4'-methylamino-2'-methoxy)phenyl]-2,6-dimethyl-5-amino benzoquinoneimine | 200 | $C_{16}H_{19}N_3O_2$ | 67.34<br>67.25 | 6.71<br>6.57 | 14.73<br>14.77 | |
| 68 | N-[(4'-methylamino-2'-methyl)phenyl]2-methyl-5-amino benzoquinoneimine | 140 | $C_{15}H_{17}N_3O.0.5H_2O$ | 68.16<br>68.35 | 6.86<br>6.99 | 15.90<br>16.11 | |
| 69 | N-[(4'-methylamino-2'-methyl)phenyl]-2,6-dimethyl-5-amino benzoquinoneimine | 149 | $C_{16}H_{19}N_3O$ | 71.34<br>71.30 | 7.11<br>7.03 | 15.60<br>15.59 | |
| 70 | N-[(4'-methylamino-2'-chloro)phenyl]-2,6-dimethyl benzoquinoneimine | 138 | $C_{15}H_{15}N_2OCl$ | 65.57<br>65.56 | 5.50<br>5.74 | 10.20<br>10.35 | 12.91<br>12.76 |
| 71 | N-[(4'-methylamino-2'-methyl)phenyl]-2-methyl-5-acetylamino benzoquinoneimine | 175 | $C_{17}H_{19}N_3O_2$ | 68.66<br>68.66 | 6.44<br>6.63 | 14.13<br>14.35 | |
| 72 | N-[(4'-methylamino-3'-methyl)phenyl]-2,6-dimethyl-5-amino benzoquinoneimine | 152 | $C_{16}H_{19}N_3O$ | 71.34<br>71.20 | 7.11<br>7.01 | 15.60<br>15.73 | |
| 73 | N-[(4'-methylamino-3'-methyl)phenyl]-2-methyl-5-acetylamino benzoquinoneimine | 210 | $C_{17}H_{19}N_3O$ | 68.66<br>68.64 | 6.44<br>6.49 | 14.13<br>14.28 | |
| 74 | N-[(4'-methylamino-3'-methyl)phenyl]-2-methyl-5-amino benzoquinoneimine | 166 | $C_{15}H_{17}N_3O$ | 70.56<br>70.33 | 6.71<br>6.72 | 16.46<br>16.34 | |
| 75 | N-[(4'-methylamino)phenyl]-2-methyl-5-acetylamino benzoquinoneimine | 161 | $C_{16}H_{17}N_3O_2$ | 67.82<br>67.72 | 6.05<br>6.18 | 14.83<br>14.92 | |
| 76 | N-[(4'methylamino-3'-methoxy)phenyl]-2-methyl-5-carbethoxyamino benzoquinoneimine | 179 | $C_{18}H_{21}N_3O_4$ | 62.96<br>63.02 | 6.16<br>6.28 | 12.24<br>12.06 | |
| 77 | N-[(4'-methylamino-3'-chloro)phenyl]-2-methyl-5-ureido benzoquinoneimine | 228 | $C_{15}H_{15}N_4O_2Cl$ | 56.51<br>56.61 | 4.71<br>4.90 | 17.58<br>17.63 | 11.14<br>10.93 |
| 78 | N-[(4'-β-hydroxyethylamino-3'-chloro)phenyl]-2,6-dimethyl-3-ureido benzoquinoneimine | 195 | $C_{17}H_{19}N_4O_3Cl$ | 56.30<br>56.41 | 5.24<br>5.34 | 15.42<br>15.33 | 9.79<br>9.81 |
| 79 | N-[(4'-β-hydroxyethylamino-3'-chloro)phenyl]-3-ureido benzoquinoneimine | 280 | $C_{15}H_{15}N_4O_3Cl$ | 53.81<br>53.86 | 4.48<br>4.71 | 16.74<br>16.62 | 10.61<br>10.36 |
| 80 | N-[(4'-β-hydroxyethylamino-3'-chloro)phenyl]-3-acetylamino benzoquinoneimine | 178 | $C_{16}H_{16}N_3O_3Cl$ | 57.57<br>57.39 | 4.79<br>4.79 | 12.59<br>12.71 | 10.64<br>10.48 |
| 81 | N-[(4'-β-hydroxyethylamino-3'-chloro)phenyl]-2-methyl-5-acetylamino benzoquinoneimine | 176 | $C_{17}H_{18}N_3O_3Cl$ | 58.70<br>58.83 | 5.18<br>5.19 | 12.08<br>12.17 | 10.21<br>10.36 |
| 82 | N-[(4'-β-hydroxyethylamino-3'-chloro)phenyl]-2-methyl-5-ureido benzoquinoneimine | 240 | $C_{16}H_{17}N_4O_3Cl$ | 55.09<br>54.84<br>54.83 | 4.88<br>4.97<br>4.91 | 16.07<br>16.03<br>16.00 | 10.18<br>10.18<br>10.30 |

(1) Double melting point

| Ex. No. (1) | BENZOQUINONEIMINE (2) | Melting Point (° C)(3) | Empirical Formula (4) | C % (5) | H % (6) | N % (7) | Cl % (8) | S % (9) |
|---|---|---|---|---|---|---|---|---|
| 83 | N-[(4'-methylamino)phenyl]-2-methyl-5-carbamylmethylamino benzoquinoneimine | 228 | $C_{16}H_{18}N_4O_2 \cdot H_2O$<br><br>MW 298 (1)<br>304 (2) | | | 17.71<br><br>17.40 | | |
| 84 | N-[(4'-methylamino-2'-methyl)phenyl]-2-methyl-5-carbamylmethylamino benzoquinoneimine | 200 | $C_{17}H_{20}N_4O_2$<br><br>MW 312 (1)<br>315 (2) | | | 17.94<br>17.58<br>17.68 | | |

TABLE I-continued

| | | | | | | | | |
|---|---|---|---|---|---|---|---|---|
| 85 | N-[(4'-methylamino-3'-methyl)phenyl]-2-methyl-5-carbamylmethylamino benzoquinoneimine | 240 | $C_{17}H_{20}N_4O_2$ | 65.36<br>65.18 | 6.45<br>6.60 | 17.94<br>18.10 | | |
| 86 | N-[(4'-β-acetylaminoethylamino-3'-chloro)phenyl]-2-methyl-5-carbamylmethylamino benzoquinoneimine | 230 with decomposition | $C_{19}H_{22}N_5O_3Cl$ | 56.50<br>56.20 | 5.45<br>5.53 | 17.35<br>17.45 | | |
| 87 | N-[(4'-β-mesylaminoethylamine-3'-chloro)phenyl]-2-methyl-5-carbamylmethylamino benzoquinoneimine | 203 with decomposition | $C_{18}H_{22}N_5O_4SCl.H_2$ | 47.21<br>47.34 | 5.28<br>5.15 | 15.30<br>14.98<br>7.70<br>7.20 | 7.74<br>7.78 | 6.99<br>7.03 |
| 88 | N-[(4'-β-hydroxyethylamino)phenyl]2-methyl-5-carbamylmethylamino benzoquinoneimine | 235 with decomposition | $C_{17}H_{20}N_4O_3.H_2O$ | 58.94<br>59.15 | 6.40<br>6.26 | 16.18<br>16.33 | | |
| 89 | N-[(4'-β-mesylaminoethylamino-3'-methyl)phenyl]-2-methyl-5-carbamylmethylamino benzoquinoneimine | 215 with decomposition | $C_{19}H_{25}N_5O_4S$ | 54.40<br>54.26 | 6.01<br>5.90 | 16.70<br>16.57 | | |
| 90 | N-[(4'-methylamino-3'-chloro)phenyl]2-methyl-5-carbamylmethylamino benzoquinoneimine | 120<br>212(3) | $C_{16}H_{17}N_4O_2Cl.H_2O$ | 54.78<br>54.67 | 5.46<br>5.16 | 16.26<br>16.53 | 10.11<br>10.13 | |
| 91 | N-[(4'-β-mesylaminoethylamino-3'-chloro)phenyl]-2-methyl-5-ureido benzoquinoneimine | 228 | $C_{17}H_{20}N_5O_4SCl$ | 47.94<br>47.78 | 4.70<br>4.74 | 16.45<br>16.63 | 8.34<br>8.54<br>8.47 | 7.50<br>7.52<br>7.56 |
| 92 | N-[(4'-β-mesylaminoethylamino-3'-chloro)phenyl]-3-ureido benzoquinoneimine | 253 | $C_{16}H_{18}N_5O_4S\ Cl$ | | | | 8.62<br>8.70<br>8.79 | 7.72<br>7.94 |
| 93 | N-[(4'-methylamino-3'-chloro)phenyl]-3-acetylamino benzoquinoneimine | 198 | $C_{15}H_{14}N_3O_2Cl$ | 59.31<br>59.21 | 4.61<br>4.81 | 13.84<br>13.93 | | |
| 94 | N-[(4'-ethylamamino-3'-methyl)phenyl]-2-methyl-5-acetylamino benzoquinoneimine | 185 | $C_{18}H_{21}N_3O_2$ | 69.45<br>69.20 | 6.75<br>7.00 | 13.50<br>13.74 | | |
| 95 | N-[(4'-β-hydroxyethylamino-3'-chloro)phenyl]-2,6-dimethyl-3-acetylamino benzoquinoneimine | 98 | $C_{18}H_{20}N_3O_3Cl$ | 59.75<br>59.44 | 5.53<br>5.77 | 11.61<br>11.61 | | |
| 96 | N-[(4'-methylamino-3'-chloro)phenyl]-2,6-dimethyl-3-ureido benzoquinoneimine | 218 | $C_{16}H_{17}N_4O_2Cl$ | 57.74<br>57.77 | 5.11<br>5.45 | 16.84<br>16.90 | | |
| 97 | N-[(4'-β-hydroxyethylamino-3'-chloro)phenyl]-2-methyl-5-carbamylmethylamino benzoquinoneimine | 170 | $C_{17}H_{19}N_4O_3Cl.H_2O$ | 53.63<br>53.65 | 5.51<br>5.38 | 14.71<br>14.94 | | |
| 98 | N-[(4'-mesylaminoethylamino-3'-chloro)phenyl]-3-acetylamino benzoquinoneimine | 230 | $C_{17}H_{19}N_4O_4S\ Cl$ | 49.69<br>49.95 | 4.63<br>4.82 | 13.64<br>13.54 | | 7.80<br>7.76 |
| 99 | N-[(4'-methylamino-3'-chloro)phenyl]-3-ureido benzoquinoneimine | 258 | $C_{14}H_{13}N_4O_2Cl$ | 55.17<br>55.14 | 4.27<br>4.56 | 18.39<br>18.64 | 11.66<br>11.57 | |

(1) molecular weight calculated
(2) molecular weight determined by potentiometric titration in acetic acid using perchloric acid
(3) double melting point

TABLE II

| Ex. No. (1) | ANILINE (Substituted) (10) | PHENOL (11) | Molar Ratio (11):(10) (12) | Reaction Medium (13) 1:1 vol ratio | Oxidizing Agent (14) | Molar Ratio (14):(11) (15) | Reaction Temp. (C°) (16) |
|---|---|---|---|---|---|---|---|
| 1 | 4-nitroso-N-ethylaniline hydrochloride | 2-methyl-5-carbamyl-methylamino phenol | 1:1 | Ethanol-water | | | 50° |
| 2 | 3-methyl-4-nitroso-N-ethylaniline | 2,6-dimethyl-3-amino phenol hydrochloride | 1:1 | " | | | 45° |
| 3 | " | 2-methyl-5-amino phenol | 1:1 | " | | | 50° |
| 4 | 4-nitroso-N-ethylaniline hydrochloride | 2-chloro-5-amino phenol | 1:1 | " | | | 40° |
| 5 | 2-methyl-4-nitroso-N-ethylaniline | 2,6-dimethyl-3-amino phenol hydrochloride | 1:1 | " | | | 40° |
| 6 | 4-nitroso N-ethylaniline hydrochloride | " | 1:1 | " | | | 40° |
| 7 | 2,5-dimethyl-4-nitroso-N-methylaniline hydrochloride | " | 1:1 | " | | | 50-60° |
| 8 | 4-nitroso-N-methylaniline | 2-methyl-5-amino phenol | 1:1 | " | | | 45° |
| 9 | 2-methoxy-4-amino-N-methylaniline sulfate | 2,6-dimethyl phenol | 1:1 | Acetone-water | Ammonium persulfate | 2:1 | 0 |
| 10 | N-methyl paraphenylenediamine dihydrochloride | 2,6-dimethyl-3-amino phenol hydrochloride | 1:1 | " | " | 1:1 | 0 |
| 11 | 3-methyl-4-amino-N-ethylaniline dihydrochloride | 3-chloro-6-ureido phenol | 1:1 | Isopropanol-water | Ammonium persulfate | 1:1 | 0 |
| 12 | 2-chloro-4-amino-N-butylaniline sulfate | 2-methyl-5-acetylamino phenol | 1:1 | acetone-water | " | 1:1 | 3 |
| 13 | 3-methyl-4-amino-N-ethylaniline dihydro- | 3-ureido | 1:1 | " | " | 1:1 | 0 |

TABLE II-continued

| Ex. No. (1) | ANILINE (Substituted) (10) | PHENOL (11) | Molar Ratio (11):(10) (12) | Reaction Medium (13) 1:1 vol ratio | Oxidizing Agent (14) | Molar Ratio (14):(11) (15) | Reaction Temp. (C°) (16) |
|---|---|---|---|---|---|---|---|
| 14 | N-methyl paraphenylenediamine dihydrochloride | phenol 2,6-dimethyl 3-acetylamino phenol | 1:1 | " | " | 1:1 | 0 |
| 15 | 3-methyl-4-amino-N-ethylaniline dihydrochloride | 3-chloro-6-acetylamino phenol | 1:1 | " | " | 2:1 | 0 |
| 16 | N-ethyl paraphenylenediamine dihydrochloride | 2-methyl-5-acetylamino phenol | 1:1 | " | " | 1:1 | 0 |
| 17 | 2-chloro-4-amino-N-butylaniline sulfate | 3-acetylamino phenol | 1:1 | " | " | 1:1 | 0 |
| 18 | N-ethyl paraphenylenediamine dihydrochloride | 2-chloro-5-acetylamino phenol | 1:1 | water | " | 2:1 | 0 |
| 19 | 2-chloro-4-amino-N-ethylaniline sulfate | 2-methyl-5-acetylamino phenol | 1:1 | acetone-water | " | 1:1 | 0 |
| 20 | 4-amino-N-($\beta$-acetylamino) ethylaniline sulfate | 3-methyl-6-chloro phenol | 1:1 | Isopropanol-water | " | 2:1 | 0 |
| 21 | 4-amino-N-($\beta$-hydroxyethyl) aniline sulfate | 2-bromo-5-amino phenol | 1:1 | Isopropanol-water | Ammonium persulfate | 2:1 | 0 |
| 22 | 2-methyl-4-amino-N-($\beta$-hydroxyethyl) aniline sulfate | 2-methyl-5-acetylamino phenol | 1:1 | Acetone-water | " | 2:1 | 0 |
| 23 | 4-amino-N-($\beta$-morpholinoethyl) aniline | 2-chloro-5-acetylamino phenol | 1:1 | " | " | 2:1 | 0 |
| 24 | 4-amino-N-($\beta$-morpholinoethyl) aniline | 3-ureido phenol | 2:1 | Isopropanol-water | Potassium ferricyanide | 4:1 | 0 |
| 25 | 4-amino-N-($\beta$-mesylaminoethyl) aniline sulfate | 2-methyl-5-acetylamino phenol | 1:1 | " | Ammonium persulfate | 2:1 | 0 |
| 26 | 4-amino-N-($\beta$-acetylaminoethyl) aniline sulfate | 3-chloro-6-ureido phenol | 1:1 | " | " | 2:1 | 0 |
| 27 | 2-methoxy-4-amino-N-($\beta$-hydroxyethyl) aniline sulfate | 2-methyl-5-amino phenol | 1:1 | " | " | 1:1 | +5 |
| 28 | 2-methyl-4-amino-N-($\beta$-mesylaminoethyl) aniline sulfate | 2,6-dimethyl-5-acetylamino phenol | 1:1 | Acetone-water | " | 1:1 | 0 |
| 29 | 2-methoxy-4-amino-N-($\beta$-acetylaminoethyl) aniline sulfate | 2,6-dimethyl 5-amino phenol hydrochloride | 1:1 | Water | " | 1:1 | 0 |
| 30 | 2-chloro-4-amino-N-($\beta$mesylaminoethyl) aniline sulfate | 2-methyl-5-acetylamino phenol | 1:1 | Acetone-water | " | 2:1 | 0 |
| 31 | 2-chloro-4-amino-N-($\beta$-acetylaminoethyl) aniline sulfate | 2,6-dimethyl phenol | 1:1 | Acetone-water | Ammonium persulfate | 2:1 | 0 |
| 32 | 2-methoxy-4-amino-N-($\beta$-hydroxyethyl) aniline sulfate | 2,6-dimethyl-5-amino phenol hydrochloride | 1:1 | Water | " | 2:1 | 0 |
| 33 | 2-methoxy-4-amino-N-($\beta$-hydroxyethyl) aniline sulfate | 2,6-dimethyl-5-acetylamino phenol | 1:1 | Acetone-water | " | 1.1:1 | 0 |
| 34 | 2-chloro-4-amino-N-($\beta$-hydroxyethyl) aniline sulfate | 3-chloro-6-acetylamino phenol | 1:1 | " | " | 1:1 | 0 |
| 35 | 2-methyl-4-amino-5-methoxy N-($\beta$-aminoethyl) aniline trihydrochloride | 2,6-dimethyl-3-amino phenol hydrochloride | 1:1 | Ethanol-water | " | 2:1 | 0 |
| 36 | 2-methyl-4-amino- N-($\beta$-mesylaminoethyl) aniline sulfate | 2-methyl-5-acetylamino phenol | 1:1 | Acetone-water | " | 2:1 | 0 |
| 37 | 2-methyl-4-amino-N-(acetylaminoethyl) aniline sulfate | 3-ureido phenol | 1:1 | " | " | 2:1 | 0 |
| 38 | 2-methyl-4-amino-N-(carbamylmethyl aniline hydrobromide | 2,6-dimethyl-3-acetylamino phenol | 1:1 | Water | " | 2:1 | 0 |
| 39 | 2-chloro-4-amino-N($\Gamma$-morpholinopropyl) aniline trihydrochloride | 3-chloro-6-acetylamino phenol | 1:1 | Acetone-water | " | 2:1 | 20 |
| 40 | N-methyl paraphenylenediamine dihydrochloride | 2,6-dimethyl phenol | 1:1 | Acetone-water | Ammonium persulfate | 2:1 | 15 |
| 41 | 2-methyl-4-amino-N-methyl aniline sulfate | 2,6-dimethyl-3-acetylamino phenol | 1:1 | " | " | 2:1 | 10 |
| 42 | 3-methyl-4-amino N-methylaniline dihydrochloride | 2,6-dimethyl-5-acetylamino phenol | 1:1 | Isopropanol-water | " | 1:1 | 5 |
| 43 | 2-methyl-4-amino-N-methylaniline sulfate | 2,6-dimethyl phenol | 1:1 | acetone-water | " | 2:1 | 15 |
| 44 | Monohydrate of 3-methyl-4-amino-N-methylaniline dihydrochloride | 2,6-dimethyl phenol | 1:1 | " | " | 2:1 | 5 |
| 45 | 3-methoxy-4-amino-N-($\beta$-hydroxyethyl) aniline sulfate | 2-methyl-5-acetylamino phenol | 1:1 | " | " | 2:1 | 15 |

TABLE II-continued

| Ex. No. (1) | ANILINE (Substituted) (10) | PHENOL (11) | Molar Ratio (11):(10) (12) | Reaction Medium (13) 1:1 vol ratio | Oxidizing Agent (14) | Molar Ratio (14):(11) (15) | Reaction Temp. (C°) (16) |
|---|---|---|---|---|---|---|---|
| 46 | 2-chloro-4-amino-N-(β-acetylaminoethyl) aniline sulfate | 3-methoxy phenol | 1:1 | " | " | 2:1 | 0 |
| 47 | N-(β-mesylaminoethyl)paraphenylenediamine sulfate | 2,6-dimethyl-3-acetylamino phenol | 1:1 | " | " | 1:1 | 5 |
| 48 | N-(β-hydroxyethyl)paraphenylenediamine sulfate | 2-methyl-5-acetylamino phenol | 1:1 | " | " | 2:1 | 5 |
| 49 | 2-methoxy-4-amino N-(β-hydroxyethyl) aniline sulfate | 2,6-dimethyl phenol | 1:1 | Isopropanol-water | " | 2:1 | 10 |
| 50 | 2-chloro-4-amino-N-(γ-morpholino propyl) aniline trihydrochloride | 2-bromo-5-amino phenol | 1:1 | Acetone-water | Ammonium persulfate | 2:1 | 20 |
| 51 | 3-methoxy-4-amino N-methylaniline dihydrochloride | 2,6-dimethyl-5-acetylamino phenol | 1:0.85 | " | " | 2:1 | 0 |
| 52 | 3-methoxy-4-amino-N-methylaniline dihydrochloride | 2-methyl-5-acetylamino phenol | 1:0.85 | Isopropanol-water | Potassium ferricyanide | 2:1 | 0 |
| 53 | Dihydrate of 2-methoxy-4-amino-N-methylaniline sulfate | 2,6-dimethyl-5-amino phenol | 1:1 | Water | Ammonium persulfate | 2:1 | 0 |
| 54 | 3-methoxy-4-amino-N-methylaniline dihydrochloride | 2-methyl-5-amino phenol | 1:0.85 | Water-isopropanol | Potassium ferricyanide | 2:1 | 0 |
| 55 | 2-chloro-4-amino-N-methylaniline sulfate | 2-methyl-5-acetylamino phenol | 1:1 | Acetone-water | Ammonium persulfate | 2:1 | 1: |
| 56 | 2-chloro-4-amino-N-methylaniline sulfate | 2,6-dimethyl-5-acetylamino phenol | 1:1 | " | " | 2:1 | 5 |
| 57 | 2-chloro-4-amino-N-methylaniline sulfate | 2,6-dimethyl phenol | 1:1 | " | " | 2:1 | 10 |
| 58 | 2-chloro-4-amino-N-methylaniline sulfate | 2,6-dimethyl-5-amino phenol hydrochloride | 1:1.10 | " | $H_2O_2$ | 8:1 | 20 |
| 59 | 2-chloro-4-amino-N-methylaniline sulfate | 2-methyl-5-amino phenol | 1:1.10 | " | " | 8:1 | 20 |
| 60 | Monohydrate of 3-chloro-4-amino-N-methylaniline dihydrochloride | 2,6-dimethyl-5-acetylamino phenol | 1:1 | Acetone-water | Ammonium persulfate | 2:1 | 5 |
| 61 | Monohydrate of 3-chloro-4-amino-N-methylaniline dihydrochloride | 2,6-dimethyl-5-amino phenol hydrochloride | 1:1 | " | " | 1:1 | 5 |
| 62 | Monohydrate of 3-chloro-4-amino-N-methylaniline dihydrochloride | 2-methyl-6-amino phenol | 1:1 | " | " | 1:1 | 5 |
| 63 | Monohydrate of 3-chloro-4-amino-N-methylaniline dihydrochloride | 2-methyl-5-acetylamino phenol | 1:0.65 | " | " | 2:1 | 5 |
| 64 | Dihydrate of 2-methoxy-4-amino-N-methylaniline sulfate | 2,6-dimethyl-5-acetylamino phenol | 1:1 | " | " | 1:1 | 0 |
| 65 | 3-chloro-4-amino-N-methylaniline dihydrochloride | 2-methyl-5-N-β-hydroxyethylamino phenol | 1:1 | Ethanol-water | " | 1:1 | 0 |
| 66 | 3-methoxy-4-amino-N-methylaniline dihydrochloride | 2,6-dimethyl phenol | 1:1 | Acetone-water | " | 2:1 | 0 |
| 67 | 3-methoxy-4-amino-N-methylaniline dihydrochloride | 2,6-dimethyl-5-amino-phenol hydrochloride | 1:0.85 | " | " | 1.75:1 | 0 |
| 68 | Monohydrate of 3-methyl-4-amino-N-methylaniline dihydrochloride | 2-methyl-5-amino phenol | 1:1 | Acetone-water | Ammonium persulfate | 2:1 | 0 |
| 69 | Monohydrate of 3-methyl-4-amino-N-methylaniline dihydrochloride | 2,6-dimethyl-5-amino phenol hydrochloride | 1:1 | " | " | 2:1 | 5 |
| 70 | 3-chloro-4-amino-N-methylaniline dihydrochloride | 2,6-dimethyl phenol | 1:1 | " | " | 2:1 | 5 |
| 71 | Monohydrate of 3-methyl-4-amino-N-methylaniline dihydrochloride | 2-methyl-5-acetylamino phenol | 1:1 | " | " | 1:1 | 5 |
| 72 | 2-methyl-4-amino-N-methylaniline sulfate | 2,6-dimethyl-5-amino phenol hydrochloride | 1:1 | " | " | 1:1 | 5 |
| 73 | " | 2-methyl-5-acetylamino phenol | 1:1 | " | " | 2:1 | 10 |

TABLE II-continued

| Ex. No. (1) | ANILINE (Substituted) (10) | PHENOL (11) | Molar Ratio (11):(10) (12) | Reaction Medium (13) 1:1 vol ratio | Oxidizing Agent (14) | Molar Ratio (14):(11) (15) | Reaction Temp. (C°) (16) |
|---|---|---|---|---|---|---|---|
| 74 | '' | 2-methyl-5-amino phenol | 1:1 | '' | '' | 2:1 | 10 |
| 75 | 4-amino-N-methylaniline dihydrochloride | 2-methyl-5-acetylamino phenol | 1:1 | '' | '' | 1:1 | 0 |
| 76 | 2-methoxy-4-amino-N-methylaniline sulfate | 2-methyl-5-carbethoxy-amino phenol | 1:1 | Acetone-water | Ammonium persulfate | 2:1 | 0 |
| 77 | 2-chloro-4-amino-N-methylaniline sulfate | 2-methyl-5-ureido phenol | 1:1 | Propanol-water | '' | 2:1 | 0 |
| 78 | 2-chloro-4-amino-N-β-hydroxyethylaniline sulfate | 2,6-dimethyl 3-ureido phenol | 1:1 | Acetone-water | '' | 2:1 | 0 |
| 79 | '' | 3-ureido phenol | 1:1 | '' | '' | 2:1 | 0 |
| 80 | '' | 3-acetyl-amino phenol | 1:1 | Isopropanol-water | '' | 2:1 | 0 |
| 81 | '' | 2-methyl-5-acetylamino phenol | 1:1 | '' | '' | 2:1 | 0 |
| 82 | '' | 2-methyl-5-ureido phenol | 1:1 | '' | '' | 2:1 | 0-5 |
| 83 | 4-amino N-methylaniline dihydrochloride | 2-methyl 5-carbamylmethylamino phenol | 1:1 | Acetone-water | '' | 2:1 | 0 |
| 84 | 3-methyl-4-amino-N-methylaniline dihydrochloride | '' | 1:1 | '' | '' | 2:1 | 0 |
| 85 | 2-methyl-4-amino-N-methylaniline dihydrochloride | '' | 1:1 | '' | '' | 2:1 | 0 |
| 86 | 2-chloro-4-amino-N-(acetylaminoethyl) aniline sulfate | 2-methyl 5-carbamylmethylamino phenol | 1:1 | Acetone-water | Ammonium persulfate | 2:1 | 0-5 |
| 87 | 2-chloro-4-amino-N-mesylaminoethyl-aniline sulfate | '' | 1:1 | '' | '' | 2:1 | 5 |
| 88 | 4-amino-N-β-hydroxyethylaniline sulfate | '' | 1:1 | '' | '' | 2:1 | 0 |
| 89 | 2-methyl-4-amino-N-mesylaminoethylaniline sulfate | '' | 1:1 | '' | '' | 2:1 | 5 |
| 90 | 2-chloro-4-amino-N-methylaniline sulfate | '' | 1:1 | '' | '' | 2:1 | 0 |
| 91 | 2-chloro-4-amino-N-(mesylaminoethyl) aniline sulfate | 2-methyl-5-ureido phenol | 1:1 | '' | '' | 2:1 | 0 |
| 92 | 2-chloro-4-amino-N-(mesylaminoethyl) aniline sulfate | 3-ureido phenol | 1:1 | '' | '' | 2:1 | 5 |
| 93 | 2-chloro-4-amino-N-(methylaniline sulfate) | 3-acetyl-amino phenol | 1:1 | '' | '' | 2:1 | 5 |
| 94 | 2-methyl-4-amino N-ethylaniline sulfate | 2-methyl-5-acetylamino phenol | 1:1 | '' | '' | 2:1 | 5 |
| 95 | 2-chloro-4-amino-N-β-hydroxy-ethylaniline sulfate | 2,6-dimethyl-3-acetyl-amino phenol | 1:1 | '' | '' | 1:1 | 0 |
| 96 | 2-chloro-4-amino-N-methylaniline sulfate | 2,6-dimethyl-3-ureido phenol | 1:1 | '' | '' | 2:1 | 5 |
| 97 | 2-chloro-4-amino-N-β-hydroxyethylaniline sulfate | 2-methyl-5-N-carbamyl-methylamino phenol | 1:1 | Acetone-water | Ammonium persulfate | 2:1 | 0 |
| 98 | 2-chloro-4-amino-N-mesylaminoethylaniline sulfate | 3-acetyl-amino phenol | 1:1 | '' | '' | 2:1 | 5 |
| 99 | 2-chloro-4-amino-N-methylaniline sulfate | 3-ureido phenol | 1:1 | '' | '' |  | 5 |

TABLE III

| (11) Ex. No. | (12) DYE Ex.No. | (13) Wt.% | (14) POLYMER Type | (15) M.W. | (16) (cps) | (17) % | (18) ALCOHOL Type | (19) % | (20) pH | (21) Hair | (22) Color Achieved |
|---|---|---|---|---|---|---|---|---|---|---|---|
| M 1 | 10 | 0.5 | VA/CA 90/10 | 10,000 |  | 2 | Ethanol | 50 | 7.8 | B 95 (1) | violine |
| M 2 | 4 | 0.1 | '' | 10,000 |  | 1 | '' | 36 | 8.1 | D (2) | silvery glycine |
| M 3 | 5 | 0.05 | PVP | 40,000 |  | 2 | Isopropanol | 25 | 9 | D | parme |
| M 4 | 12 | 0.008 | VA/CA 90/10 | 10,000 |  | 2 | Ethanol | 50 | 8.1 | D | pale pearly rose mauve |
| M 5 | 15 | 0.025 | VP/VA 30/70 | 160,000 |  | 2 | '' | 40 | 8.8 | D | emerald green |
| M 6 | 19 | 0.004 | VA/CA 90/10 | 25,000 |  | 1 | '' | 36 | 8.4 | D | light pink blonde |
| M 7 | 2 | 0.05 | PVP | 160,000 |  | 2 | Isopropanol | 25 | 9 | D | pearly mauve |
| M 8 | 17 | 0.01 | VP/VA 60/40 |  | 4 | 2 | '' | 35 | 9.6 | D | very light silver |
| M 9 | 1 | 0.05 | VA/CA 90/10 | 25,000 |  | 1 | Ethanol | 20 | 9.5 | D | pale silvery mauve |
| M 10 | 18 | 0.1 | VP/CA 30/70 | 160,000 |  | 2 | '' | 40 | 10.2 | D | pearly turquoise blue |

TABLE III-continued

| (11) Ex. No. | (12) DYE Ex.No. | (13) Wt.% | (14) POLYMER Type | (15) M.W. | (16) (cps) | (17) % | (18) ALCOHOL Type | (19) % | (20) ph | (21) Hair | (22) Color Achieved |
|---|---|---|---|---|---|---|---|---|---|---|---|
| M 11 | 5 | 0.002 | " | " | | 2 | " | 40 | 5.7 | D | light pink blond |
| M 12 | 18 | 0.1 | " | " | | 2 | " | 40 | 10.2 | B 95 | silvery eucalyptus green |
| M 13 | 14 | 0.1 | VA/CA 90/10 | 25,000 | | 1 | " | 36 | 8.5 | D | very luminous gentian |
| M 14 | 10 | 0.2 | " | 25,000 | | 2 | " | 50 | 7.4 | D | purple |
| M 15 | 3 | 0.1 | VP/VA 60/40 | | 3.3 | 2 | Isopropanol | 35 | 9.8 | B 95 | beige grey with violet glints |
| M 16 | 16 | 0.02 | VP/VA 70/30 | 40,000 | | 3 | Ethanol | 25 | 8.7 | D | ice-blue |
| M 17 | 10 | 0.002 | " | " | | 3 | " | 25 | 10.1 | " | pearly pale pink |
| M 18 | 9 | 0.015 | VP/VA 30/70 | 160,000 | | 2 | " | 40 | 9.3 | " | pearly light blue |
| M 19 | 13 | 0.013 | VP/VA 60/40 | | 3.7 | 2 | Isopropanol | 35 | 9.3 | " | light turquoise blue |
| M 20 | 6 | 0.05 | MM/StM/DEM 20/23/57 | | 8 | 2.5 | Ethanol | 30 | 8 | " | deep violet pink |
| M 21 | 18 | 0.1 | VP/VA 30/70 | 160,000 | | 2 | " | 40 | 10.2 | " | deep chestnut with bronze glints |
| M 22 | 14 / 10 / C₁(3) | 0.05 / 0.1 / 0.08 | VA/CA 90/10 | 50,000 | | 2 | " | 50 | 6.7 | D | deep violet |
| M 23 | 14 / 10 / C₁(3) / C₂(4) | 0.05 / 0.002 / 0.15 / 0.12 | VA/CA 90/10 | 70,000 | | 2 | " | 50 | 7.5 | D | golden light chestnut with violet glints |
| M 24 | 7 | 0.2 | MM/StM/DEM | | 12 | 2.5 | " | 30 | 10.5 | B 95 | tin grey with light violet glints |
| M 25 | 28 | 6.09 | VA/CA 90/10 | 25,000 | | 2 | " | 50 | 6.3 | D | silvery glycine |
| M 26 | 30 | 0.09 | VP/VA 60/40 | | 4 | 2 | Isopropanol | 35 | 8.1 | D | silvery blue grey |
| M 27 | 20 | 0.009 | VP/VA 70/30 | 40,000 | | 3 | Ethanol | 25 | 8.5 | D | pearly light green |
| M 28 | 34 | 0.02 | VP/VA 60/40 | | 4 | 2 | Isopropanol | 35 | 9.4 | D | pearly light blue |
| M 29 | 32 | 0.02 | " | | 3.3 | 2 | " | 35 | 5.5 | D | light parme |
| M 30 | 31 | 0.05 | " | | 3.7 | 2 | " | 35 | 9 | D | silvery grey with mauve glints |
| M 31 | 23 | 0.015 | PVP | 360,000 | | 2 | " | 25 | 8.9 | D | light green with golden glints |
| M 32 | 33 | 0.025 | VA/CA 90/10 | 50,000 | | 1 | Ethanol | 36 | 5.5 | D | pearly light blue |
| M 33 | 25 | 0.5 | " | 50,000 | | 2 | " | 50 | 10.1 | B 95 | metallic grey |
| M 34 | 35 | 0.05 | " | 70,000 | | 1 | " | 36 | 9.2 | D | silvery pale mauve |
| M 35 | 21 | 0.05 | " | 50,000 | | 2 | " | 50 | 7 | D | silvery blue grey |
| M 36 | 36 | 0.06 | " | " | | 2 | " | 50 | 8.8 | D | pearly grey |
| M 37 | 37 | 0.065 | VP/CA 60/40 | | 3.3 | 2 | Isopropanol | 35 | 9.3 | B 95 | dark blue grey |
| M 38 | 27 | 0.05 | MM/StM/DEM(5) | | 2.5 | 2.5 | Ethanol | 30 | 10.3 | D | pink beige grey |
| M 39 | 24 | 0.1 | VA/CA 90/10 | 50,000 | | 2 | " | 50 | 6.4 | D | very luminous deep violet |
| M 40 | 26 | 0.033 | VP/CA 70/30 | 40,000 | | 3 | " | 25 | 6.7 | D | pearly light blue |
| M 41 | 22 | 0.09 | VP/CA 30/70 | 160,000 | | 2 | " | 40 | 9.7 | B 95 | metallic grey |
| M 42 | 21 | 0.002 | PVP | 360,000 | | 2 | Isopropanol | 25 | 10.3 | D | very light silver with blue glints |
| M 43 | 29 | 0.045 | MM/StM/DEM(5) | | 8 | 2.5 | Ethanol | 30 | 9 | D | tamarisk pink |
| M 44 | 39 | 0.3 | PVP | 40,000 | | 2 | Isopropanol | 25 | 5.5 | D | deep royal blue |
| M 45 | 38 | 0.1 | VA/CA 90/10 | 70,000 | | 1 | Ethanol | 36 | 9 | B 95 | silvery grey with mauve glints |
| M 46 | 36 / 22 / C₃(6) / C₄(7) | 0.1 / 0.2 / 0.02 / 0.03 | VA/CA 90/10 | " | | 2 | " | 50 | 7 | B 95 | steel grey |
| M 47 | 57 | 0.25 | VP/VA 60/40 | | 3.7 | 2 | Isopropanol | 35 | 8.5 | D | silvery pale violet |
| M 48 | 60 | 0.1 | " | | 4 | 2 | " | 35 | 5.5 | D | silvery grey with light mauve glints |
| M 49 | 69 | 0.3 | VA/CA 90/10 | 45,000 | | 2 | Ethanol | 50 | 5 | D | violine |
| M 50 | 99 | 0.35 | " | " | | 2 | " | 50 | 7 | B 95 | metallic grey |
| M 51 | 94 | 0.1 | " | " | | 2 | " | 50 | 6.5 | D | very light pearly blue |
| M 52 | 66 | 0.35 | " | " | | 2 | " | 50 | 7 | D | royal blue |
| M 53 | 92 | 0.15 | VP/VA 70/30 | 40,000 | | 3 | " | 25 | 8 | D | pearly pink beige |
| M 54 | 91 | 0.15 | VA/CA 90/10 | 50,000 | | 1 | " | 36 | 7 | D | lilac |
| M 55 | 65 | 0.3 | " | " | | 2 | " | 50 | 9.5 | D | violet beige |
| M 56 | 75 | 0.1 | VP/VA 60/40 | | 4 | 2 | Isopropanol | 35 | 5 | D | silvery blue |
| M 57 | 63 | 0.05 | " | | 4 | 2 | " | 35 | 10.5 | D | cyclamen pink |
| M 58 | 59 | 0.035 | VP/VA 60/40 | | 3.5 | 2 | Isopropanol | 35 | 6 | D | salmon pink |
| M 59 | 53 | 0.05 | VP/VA 30/70 | 160,000 | | 2 | Ethanol | 40 | 6 | D | beige shaded mauve |
| M 60 | 67 | 0.09 | " | " | | 2 | " | 40 | 8.5 | D | pearly glycine |
| M 61 | 61 | 0.07 | VP/VA 60/40 | | 3.7 | 2 | Isopropanol | 35 | 9.5 | D | pearly pale pink |
| M 62 | 71 | 0.03 | VP/VA 30/70 | 160,000 | | 2 | Ethanol | 40 | 8.5 | D | pearly myosotis blue |
| M 63 | 76 | 0.05 | " | " | | 2 | " | 40 | 10 | D | light blue grey |
| M 64 | 72 | 0.2 | " | " | | 2 | " | 40 | 4.5 | D | purple |
| M 65 | 73 | 0.1 | " | " | | 2 | " | 40 | 5 | D | silvery lavender blue |
| M 66 | 88 / 26 | 0.2 / 0.15 | VP/VA 70/30 | 40,000 | | 3 | " | 20 | 8.5 | D | silvery grey violet |
| M 67 | 62 | 0.025 | VA/CA 90/10 | 70,000 | | 1 | " | 35 | 7 | D | pink beige |
| M 68 | 64 | 0.15 | " | 10,000 | | 2 | " | 50 | 7 | D | myosotis blue |
| M 69 | 68 | 0.13 | " | 50,000 | | 1 | " | 36 | 4.5 | D | violet pink |
| M 70 | 58 | 0.05 | " | " | | 2 | " | 50 | 8.5 | D | very luminous salmon pink |
| M 71 | 51 | 0.1 | " | " | | 1 | " | 36 | 7 | D | silvery grey blue |
| M 72 | 89 | 0.1 | VP/VA 60/40 | | 3.7 | 2 | Isopropanol | 35 | 4 | D | silvery glycine |
| M 73 | 88 | 0.1 | PVP | 40,000 | | 2 | " | 25 | 9 | B 95 | metallic grey with mauve glints |
| M 74 | 87 | 0.05 | VP/VA 30/70 | 160,000 | | 2 | Ethanol | 40 | 8.5 | D | golden pale pink |
| M 75 | 86 | 0.075 | VP/VA 70/30 | 40,000 | | 3 | " | 25 | 6.5 | D | eglatine |

TABLE III-continued

| (11) Ex. No. | (12) DYE Ex.No. | (13) Wt.% | (14) POLYMER Type | (15) M.W. | (16) (cps) | (17) % | (18) ALCOHOL Type | (19) % | (20) pH | (21) Hair | (22) Color Achieved |
|---|---|---|---|---|---|---|---|---|---|---|---|
| M 76 | 85 | 0.05 | VP/VA 60/40 | | 4 | 2 | Isopropanol | 35 | 4 | D | glycine |
| M 77 | 98 | 0.1 | VP/VA 30/70 | 160,000 | | 2 | Ethanol | 40 | 7 | D | light silver |
| M 78 | 56 | 0.2 | VA/CA 90/10 | 70,000 | | 1 | " | 36 | 9 | D | mauve |
| M 79 | 50 | 0.2 | " | 50,000 | | 1 | " | 36 | 5.5 | D | violet |
| M 80 | 81 | 0.2 | VP/VA 30/70 | 160,000 | | 2 | " | 40 | 4 | D | light grey with mauve glints |
| M 81 | 79 | 0.075 | VA/CA 90/10 | 50,000 | | 1 | " | 50 | 7 | D | light silvery grey shaded mauve |
| M 82 | 54 | 0.1 | " | 50,000 | | 1 | " | 50 | 7 | D | violet blue |
| M 83 | 45 | 0.1 | " | 70,000 | | 1 | " | 36 | 8 | D | silvery myosotis blue |
| M 84 | 46 | 0.1 | " | 70,000 | | 1 | " | 36 | 9 | D | pearly mauve |
| M 85 | 8 | 0.2 | VP/VA 30/70 | 160,000 | | 2 | " | 40 | 8 | D | tamarisk pink |
| M 86 | 42 | 0.1 | VA/CA 90/10 | 70,000 | | 2 | " | 50 | 6.5 | D | silvery blue grey |
| M 87 | 44 | 0.3 | " | 70,000 | | 2 | " | 50 | 6 | D | lavender blue |

(1) B 95 = 95% natural white hair
(2) D = bleached hair
(3) $C_1$ = N[4'-hydroxy)-phenyl]-2,6-dimethyl benzoquinoneimine
(4) $C_2$ = 4-nitro-N,N-di-$\beta$-hydroxyethylaniline
(5) Terpolymer of methyl methacrylate (20%)-stearyl methacrylate (23%) dimethylaminoethyl methacrylate (57%) quaternized with dimethyl sulfate and having a viscosity of 8–12 cps, at 5% in dimethylformamide and at the boiling temperature of ether.
(6) $C_3$ = Nitro-ortho p-phenylenediamine
(7) $C_4$ = 1-$\gamma$-amino propylamino anthraquinone

TABLE IV

| (31) Ex. No. | (32) DYE EX. NO. | (33) Wt. % | (34) Surface active agent Type | (35) wt. % | (36) SOLVENT Type | (37) wt. % | (38) OTHER ADJUVANTS Type | (39) wt. % | (40) pH | (41) Hair | (42) Color achieved |
|---|---|---|---|---|---|---|---|---|---|---|---|
| T 1 | 1 | 0.53 | | | Isopropanol | 40 | | | 11 | D (10) | silver with mauve glints |
| T 2 | 2 | 0.04 | | | MEDG(1) Ethanol | 5 25 | | | 9 | D | silvery mauve grey |
| T 3 | 15 | 0.077 | | | Ethanol | 23 | CMC (2) | 3.9 | 10.4 | D | emerald green |
| T 4 | 5 | | AL 10.50E (3) | 5 | Butylglycol | 5 | | | 6 | D | light pink blond |
| T 5 | 16 2 C1 (4) C2 (5) | 0.6 0.5 0.05 0.07 | " | 20 | | | | | 8.5 | D | pink beige |
| T 6 | 3 | 0.30 | LSS 19 (6) | 20 | | | EDTA (7) | 2 | 10.6 | D | silvery grey with blue glints |
| T 7 | 9 | 0.06 | | | Ethanol | 20 | CMC | 4 | 8 | D | pearly light turquoise blue |
| T 8 | 18 | 0.2 | NP 40E (8) NP 90E (9) | 10 10 | | | | | 5.6 | 395(11) | vervain |
| T 9 | 10 | 0.1 | ALS (12) | 10 | | | | | 9.7 | D | pearly light pink |
| T 10 | 16 | 0.1 | " | 10 | | | | | 10.5 | D | pearly light green |
| T 11 | 6 | 0.33 | | | Ethanol | 30 | CMC | 3 | 10.5 | B 95 | silvery violet |
| T 12 | 4 | 0.4 | AL 10.50E | 20 | | | | | 10 | " | eucalyptus green |
| T 13 | 15 C3 (14) C4 (15) C5 (16) | 0.1 0.08 0.10 0.04 | LSS 19 | 20 | | | EDTA | 2 | 10.5 | D | mahogany |
| T 14 | 11 | 0.025 | | | Isopropanol | 50 | "Carbopol 934" (17) | 2.38 | 6 | D | light green |
| T 15 | 27 | 0.07 | LSS 19 | 20 | | | EDTA | 0.2 | 10.7 | D | light beige grey |
| T 16 | 23 | 1 | NP 90E | 10 | " | 15 | | | 5.5 | B 95 | petroleum blue |
| T 17 | 20 | 0.7 | DFAC (13) | 7.5 | Ethanol | 25 | | | 7 | " | eucalyptus green |
| T 18 | 32 | 0.1 | | | " MEDG | 20 10 | | | 10.5 | D | pearly pink beige |
| T 19 | 23 20 C6 (18) C7 (19) | 0.30 0.35 0.03 0.1 | NP 40E NP 90E | 8.5 8.5 | Ethanol | 15 | | | 9 | B 95 | light chestnut with copper glints |
| T 20 | 24 | 0.4 | | | Ethanol | 40 | | | 9 | D | deep violet blue |
| T 21 | 37 | 1.1 | | | " | 45 | | | 9.5 | D | myosotis blue |
| T 22 | 33 | 0.8 | | | " | 20 | CMC | 4 | 5.5 | D | silvery light blue |
| T 23 | 37 24 C2 (5) C8 (20) | 0.3 0.2 0.09 0.05 | | | " | 40 | | | 10.5 | B 95 | silvery mauve grey |
| T 24 | 26 | 0.65 | | | " | 33 | "Carbopol 934" (17) | 3 | 10 | D | light emerald green |
| T 25 | 25 | 0.22 | NP 90E | 10 | Butylglycol | 5 | | | 5.5 | D | platinum with light blue glints |
| T 26 | 34 | 2 | DFAC (13) | 6.5 | Ethanol | 35 | | | 10.5 | D | pearly light turquoise blue |
| T 27 | 43 | 0.4 | AL 10.50E (3) | 5 | Butylglycol | 5 | | | 7 | D blue | very silvery pale |
| T 28 | 40 | 0.25 | DFAC (13) | 10 | | | | | 9.5 | D | pearly pastel blue |
| T 29 | 48 | 0.2 | ALS (12) | 10 | | | | | 9 | D | ice blue |
| T 30 | 49 | 0.4 | | | | | "Carbopol 934" (17) | 4.76 | 9.5 | D | pearly pastel blue |

TABLE IV-continued

| Ex. No. | DYE Ex. No. | Wt. % | Surface active agent Type | wt. % | SOLVENT Type | wt. % | OTHER ADJUVANTS Type | wt. % | pH | Hair | Color achieved |
|---|---|---|---|---|---|---|---|---|---|---|---|
| T 31 | 47 | 0.4 | LSS 19 (6) | 20 | | | EDTA | 0.2 | 12 | D | light bluish silver |
| T 32 | 41 | 0.05 | | | | | CMC (2) | 5 | 10 | D | very light pearly blue |
| T 33 | 90 | 0.5 | Al 10.50E (3) | 5 | | | | | 9 | D | eglantine pink |
| T 34 | 95 | 0.35 | LSS 19 (6) | 20 | | | EDTA (7) | 0.2 | 10 | D | light silver grey |
| T 35 | 93 | 0.3 | | | | | CMC (2) | 5 | 9 | D | light blue grey |
| T 36 | 96 | 0.3 | | | MEDG (1) | 10 | | | 5 | D | silvery mauve |
| T 37 | 97 | 0.4 | DFAC (13) | 10 | | | | | 9 | D | very light pink blond |
| T 38 | 78 | 0.5 | LSS 19(6) | 20 | | | EDTA (7) | 0.2 | 10 | D | mauve |
| T 39 | 52 | 0.15 | | | Ethanol | 25 | | | 9 | D | light turquoise blue |
| T 40 | 70 | 0.6 | " | 20 | | | " | 0.2 | 11 | D | pearly light beige grey |
| T 41 | 84 | 0.35 | | | " | 20 | "Carbopol 934" (17) | 3.6 | 10 | D | silvery pale mauve |
| T 42 | 83 | 0.35 | ALS (12) | 5 | | | | | 9.2 | D | light silver grey with mauve glints |
| T 43 | 74 | 0.6 | DFAC (6) | 2 | " | 30 | | | 10.5 | B 95 | metallic grey with mauve glints |
| T 44 | 55 | 0.8 | NP 40E (8) NP 90E (9) | 8 8 | " | 2 | | | 11 | D | light silver grey |
| T 45 | 80 | 0.4 | Al 10.50E (3) | 5 | Butylglycol | | | | 9 | D | silvery light blue grey |
| T 46 | 77 | 0.5 | AL10.50E(3) | 20 | | | | | 4 | D | pearly light |
| T 47 | 82 | 0.2 | | | Propylene glycol | 5 | CMC (2) | 4 | 8 | D beige | light pink ash |
| T 48 | 93 | 0.2 | | | Ethanol | 50 | " | 2.5 | 10 | B 95 | metallic grey shaded violet |
| | 87 | 0.5 | | | | | | | | | |
| | 35 | 0.1 | | | | | | | | | |

(1) MEDG = monomethyl ether of diethyleneglycol
(2) CMC = Carboxymethylcellulose
(3) Al 10.5 OE = laurylalcohol oxyethylenated with 10.5 moles of ethylene oxide
(4) C1 = 2-methoxy-4-nitro-β-hydroxyethylaniline
(5) C2 = 1-γ-aminopropylamino anthraquinone
(6) LSS 19 = mixture consisting of 19% laurylalcohol oxyethylenated with 2 moles of ethylene oxide and 81% of the sodium sulfate salt of the same oxyethylenated alcohol
(7) EDTA = ethylene diamine tetra-acetic acid
(8) NP 40E = Nonylphenol oxyethylenated with 4 moles of ethylene oxide
(9) NP 90E = Nonylphenol oxyethylenated with 9 moles of ethylene oxide
(10) D = bleached hair
(11) B 95 = 95% naturally white hair
(12) ALS = ammonium laurylsulfate
(13) DFAC = diethanolamides of fatty acids of coprah
(14) C3 = N-[(4'-hydroxy)phenyl]-2,6-dimethylbenzoquinoneimine
(15) C4 = N-[(4'-amino)phenyl] 2-methyl-5-aminobenzoquinoneimine
(16) C4 = Nitroorthophenylenediamine
(17) "Carbopol 934" = Polymer of acrylic acid having a molecular weight between 2-3 million
(18) C6 = N-[(4'-ethylamino)phenyl]-2-methyl 5-acetylamino
(19) C7 = nitroparaphenylenediamine
(20) C8 = 3-nitro-4(β-hydroxyethyl) amino anisole

We claim:

1. A composition for dyeing keratin fibers which comprises a dyeing effective amount of an indoaniline compound of the formula or a tautomeric form thereof wherein $R_1$ and $R_4$ each independently represent a member selected from the group consisting of hydrogen, halogen, alkyl having 1 to 6 carbon atoms, alkoxy having 1 to 6 carbon atoms, acetylamino and ureido, $R_2$ and $R_3$ each independently represent a member selected from the group consisting of hydrogen, halogen, alkyl having 1 to 6 carbon atoms, alkoxy having 1 to 6 carbon atoms, amino, N-alkylamino, N-(hydroxyalkyl)-amino, N-(carbamylalkyl)-amino, acetylamino and ureido, each of said alkyl moieties containing 1 to 6 carbon atoms, $R_5$ and $R_6$ each independently represent a member selected from the group consisting of hydrogen, halogen, alkyl having 1 to 6 carbon atoms and alkoxy having 1 to 6 carbon atoms with the proviso that when $R_5$ and $R_6$ are both other than hydrogen at least one is in a meta-position relative to the $NHR_7$; and $R_7$ represents a member selected from the group consisting of alkyl, hydroxyalkyl, acetylaminoalkyl, mesylaminoalkyl, carbamylalkyl, aminoalkyl and morpholinoalkyl, each of said alkyl moieties containing 1 to 6 carbon atoms and a compatible vehicle.

2. The composition according to claim 1 which contains from 0.001 to 2% by weight of said compound.

3. The composition according to claim 1 wherein the vehicle is an aqueous solution, a cream or a gel.

4. The composition according to claim 2, having a pH from 5 to 11.

5. The composition according to claim 4, having a pH from 7 to 9.

6. The composition according to claim 1, which also contains another direct hair dye.

7. The composition according to claim 6, wherein said direct hair dye is selected from the group consisting of nitrobenzene, azo, anthraquinone, indamine, indophenol and another indoaniline dye.

8. The composition according to claim 1 which also contains a member selected from the group consisting of a glycol and a wetting agent.

9. The composition according to claim 1 wherein the vehicle is an aqueous-alcoholic solution and also contains a cosmetic film-forming resin.

10. The composition according to claim 9, wherein the alcohol is a low molecular weight alcohol.

11. The composition according to claim 10, wherein said alcohol is selected from the group consisting of ethanol and isopropanol.

12. The composition according to claim 10, which contains 20 to 70% by weight of said alcohol.

13. The composition according to claim 9 which contains 1 to 3% by weight of said cosmetic film-forming resin.

14. The composition according to claim 9 wherein said cosmetic film-forming resin is selected from the group consisting of polyvinylpyrrolidone; copolymer of vinylpyrrolidone and vinyl acetate; copolymer of vinyl acetate and crotonic acid; copolymer of maleic anhydride and butyl vinyl ether; copolymer of methyl vinyl ether and maleic anhydride and the ethyl, isopropyl and butyl esters thereof; and a terpolymer of methyl methacrylate, stearyl methacrylate and dimethylaminoethyl methacrylate quaternized by dimethyl sulphate.

15. A process for dyeing living human hair comprising impregnating said hair with a composition as defined in claim 1 for 5 to 30 minutes, rinsing said hair and optionally washing said hair with a shampoo and drying said hair.

16. A process for coloring and wavesetting living human hair comprising applying to said hair which has been washed and rinsed a composition as defined in claim 9, constraining the hair in a deformed state and drying said hair.

* * * * *